United States Patent
Burgos

(10) Patent No.: US 6,953,852 B2
(45) Date of Patent: Oct. 11, 2005

(54) PREPARATION OF 3-AMINO-1,2,4-BENZOTRIAZINE DIOXIDE

(75) Inventor: Alain Burgos, Angers (FR)

(73) Assignee: Sanofi-Aventis, Paris (FR)

(*) Notice: Subject to any disclaimer, the term of this patent is extended or adjusted under 35 U.S.C. 154(b) by 0 days.

(21) Appl. No.: 10/494,728

(22) PCT Filed: Nov. 8, 2002

(86) PCT No.: PCT/EP02/13202

§ 371 (c)(1),
(2), (4) Date: Oct. 22, 2004

(87) PCT Pub. No.: WO03/042192

PCT Pub. Date: May 22, 2003

(65) Prior Publication Data

US 2005/0049412 A1 Mar. 3, 2005

Related U.S. Application Data

(60) Provisional application No. 60/338,139, filed on Nov. 13, 2001.

(51) Int. Cl.$^7$ .................. C07D 253/065; C07D 253/08; C07D 271/08
(52) U.S. Cl. ...................... 544/183; 548/125
(58) Field of Search ........................ 544/183; 548/125

(56) References Cited

U.S. PATENT DOCUMENTS 3,868,371 A 2/1975 Metzger et al.
4,866,175 A 9/1989 Issidorides et al.
5,672,702 A 9/1997 Philion

*Primary Examiner*—Venkataraman Balasubramanian
(74) *Attorney, Agent, or Firm*—Paul Dupont; Kelly Bender; Paul Darkes

(57) ABSTRACT

Industrially applicable process for preparing 3-amino-1,2,4-benzotriazine 1,4-dioxide.

13 Claims, No Drawings

PREPARATION OF 3-AMINO-1,2,4-BENZOTRIAZINE DIOXIDE

This application is a 371 of PCT/EP02/13202, filed Nov. 08, 2002, which claims benefit of U.S. Provisional Application No. 60/338,139, filed Nov. 13, 2001.

BACKGROUND OF THE INVENTION

This invention relates to a process for preparing 3-amino-1,2,4-benzotriazine 1,4-dioxide known under the nonproprietary name tirapazamine.

Tirapazamine is disclosed in U.S. Pat. No. 5,175,287 as a radiosensitizer and selective cytotoxic agent for hypoxic tumor cells, and U.S. Pat. No. 5,484,612 discloses that tirapazamine enhances the cytotoxicity of chemotherapy agents.

The preparation of tirapazamine is disclosed in *Angew. Chem.* 84, 1061 (1972) and in U.S. Pat. No. 3,868,371. The process involves reaction of benzofuroxan with disodium cyanamide in aqueous methanol followed by acidification with acetic acid to give 3-amino-1,2,4-benzotriazine 1,4-dioxide. U.S. Pat. No. 5,672,702 discloses an improved process for preparing tirapazamine of high purity which involves reaction of benzofuroxan with disodium cyanamide in aqueous dimethyl sulfoxide followed by acidification with methanesulfonic acid and crystallization from sodium acetate buffer.

The above processes are exothermic, and while controllable on a small scale, pose the risk of a dangerous runaway exothermic reaction when carried out on an industrial scale. This risk is, of course, magnified by the fact that tirapazamine is a cytotoxic agent. Reducing the scale on which the reaction is carried out in order to avoid this disadvantage, of course, defeats the purpose of an industrial production process. Moreover, even if the exothermic reaction could be controlled, the above processes are carried out in strongly basic aqueous medium, conditions under which tirapazamine is unstable. Therefore, both the yield and the purity of the resulting product are diminished. Thus, there is a need for a safe industrial process for producing tirapazamine and one in which tirapazamine is stable.

BRIEF SUMMARY OF THE INVENTION

Accordingly, the present invention provides a process for safely producing tirapazamine of high purity and in relatively high yield on an industrial scale and which furthermore avoids the use of aqueous base and the industrially undesirable materials dimethyl sulfoxide and methanesulfonic acid employed in the prior art.

Thus, the present process comprises the reaction of benzofuroxan with cyanamide in the presence of an organic base in a non-aqueous medium followed by neutralization with an organic acid.

DETAILED DESCRIPTION OF THE INVENTION

More particularly, benzofuroxan is reacted with a stoichiometric excess of cyanamide in the presence of an organic base in a non-aqueous medium at about room temperature. When the reaction is complete the reaction mixture is treated with an organic acid to give tirapazamine.

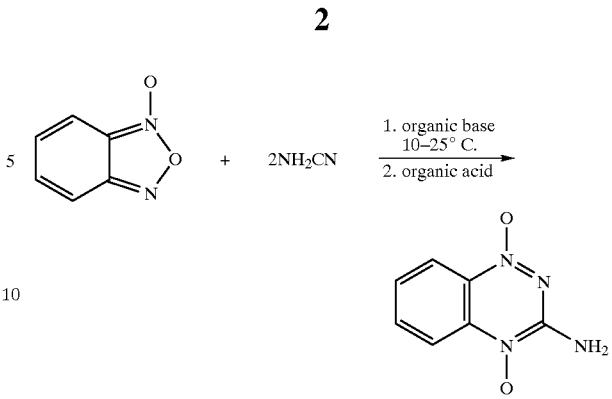

The organic base is a strong, non-nucleophilic base, preferably a hindered amine such as 1,8-diazabicyclo[5.4.0]undec-7-ene (DBU), 1,5-diazabicyclo[4.3.0]non-5-ene (DBN), and the like. DBU is preferred.

The organic acid is preferably a weak organic acid, e.g. acetic acid, which will effectively liberate tirapazamine from its organic base salt.

Benzofuroxan is reacted with cyanamide in a ratio of about 2 to 3 moles of cyanamide per mole of benzofuroxan, preferably about 2 moles of cyanamide per mole of benzofuroxan. The base, preferably DBU, is likewise used in a ratio of about 2 to 3 moles of base per mole of benzofuroxan.

The reaction is conveniently carried out at about room temperature, i.e., about 20–25° C. in the presence or absence of a solvent. In view of its exothermic nature, if the reaction is carried out without a solvent, or in concentrated solution, the temperature is preferably maintained at about 20–25° C. with cooling. Because tirapazamine is unstable to aqueous base, any solvent used should be non-aqueous and although small amounts of water are tolerated, optimum yields are obtained when the solvent, reactants and reagents are essentially water-free.

It is preferred to carry out the reaction in a non-aqueous, polar solvent such as acetone, isopropanol, acetonitrile and the like. Ordinarily, the solvent is used in a ratio of about 0.25:1 w/w to 1.5:1 w/w solvent/benzofuroxan. Acetonitrile is a preferred solvent. The reaction is allowed to proceed for up to about 170 hours, preferably about 48–72 hours, or until the reaction is essentially complete as indicated by TLC or HPLC. The resulting basic reaction mixture is neutralized by addition of an organic acid, e.g. acetic acid, in an amount of about 1 to 1.3 moles of acid per mole of base. It is advantageous to dilute and cool the reaction mixture before adding the acid in order to protect the product from degradation and to facilitate its isolation. The reaction mixture can be diluted with any inert solvent, i.e. one that does not react with the components of the reaction mixture and in which tirapazamine is relatively insoluble, e.g. acetonitrile, acetone, isopropanol, benzene, toluene and the like. Of course, if the reaction has been carried out in the presence of a solvent, the reaction mixture is conveniently diluted with more of the same solvent. The tirapazamine is allowed to precipitate and is then isolated in accordance with conventional procedures. For example, the neutralized reaction mixture is stirred at about 5–25° C. for about 2–72 hours, and the resulting precipitate is collected by filtration, washed with fresh solvent and water, and dried. Preferably, the water wash is carried out by slurrying the product in water, stirring for about 30–60 minutes and filtering the slurry. The tirapazamine so-produced ordinarily requires no further purification. However, if desired, it can be further purified by conventional purification techniques. For example, further purification can be effected by dissolving the collected tirapazamine in a strong acid, e.g., aqueous methanesulfonic acid, filtering the solution and reprecipitating tirapazamine by treatment with a weak base, e.g., sodium acetate. Conveniently, the acidic solution is added to aqueous sodium acetate and stirred at about 10–25° C. for about 1–24 hours. The precipitated tirapazamine is then collected by filtration, washed with water and dried. The starting materials, benzofuroxan and cyanamide, are known and commercially available as are the reagent bases, acids and solvents.

The invention is further illustrated by the following non-limitative examples.

EXAMPLE 1

To a suspension of 4.08 g (30 mmoles) of benzofuroxan in 4 ml of acetonitrile was added 11.4 g (75 mmoles) of DBU. To the resulting solution was added a solution containing 2.52 g (60 mmoles) of cyanamide in 6.2 ml of acetonitrile over a one-hour period. After stirring at room temperature for 6 days the reaction mixture was diluted with 30 ml of toluene, cooled to 0° C. and treated with 5.4 g (90 mmoles) of acetic acid. After stirring at room temperature overnight, the resulting precipitate was collected and washed twice with 6 ml of acetonitrile and 15 ml of water to give, after drying under vacuum overnight, 2.11 g of tirapazamine.

EXAMPLE 2

To a solution containing 3.77 g (27.7 mmoles) of benzofuroxan in 8.44 g (55.4 mmoles) of DBU was added portionwise with cooling 2.33 g (55.5 mmoles) of cyanamide. The reaction mixture was stirred at room temperature for 5 days and then diluted with 26 ml of acetone and treated with 4.16 g (69.3 mmoles) of acetic acid. After stirring at room temperature overnight the mixture was further diluted with 30.2 ml of acetone and stirred at room temperature an additional 2.5 hours. The resulting precipitate was collected and washed with 50 ml of acetone and 15 ml of water and then dried under vacuum overnight to give 2.09 g of tirapazamine.

EXAMPLE 3

A solution containing 3.35 g (80 mmoles) of cyanamide in 10 ml of isopropanol was added to a solution containing 5.43 g (40 mmoles) of benzofuroxan in 12.15 g (80 mmoles) of DBU and the resulting mixture stirred at room temperature for 4 days. HPLC indicated that reaction was incomplete. Accordingly, an additional 16.8 g (40 mmoles) of cyanamide was added portionwise to the reaction mixture and stirring at room temperature continued an additional 3 days. The mixture was then diluted with 28 ml of isopropanol and treated with 4.8 g (80 mmoles) of acetic acid. After stirring at room temperature overnight the resulting precipitate was collected and washed twice with 15 ml of isopropanol and 20 ml of water to afford, after drying overnight under vacuum, 3.39 g of tirapazamine.

EXAMPLE 4

To a solution containing 100 g (0.73 mole) of benzofuroxan in 223.6 g (1.5 moles) of DBU was added a solution containing 61.7 g (1.5 moles) of cyanamide in 38 ml of acetonitrile while maintaining the temperature between 20 and 25° C. The reaction mixture was stirred at that temperature for 50 hours after which it was diluted with 662 ml of acetonitrile, cooled to 15° C. and treated with 88.2 g (1.5 moles) of acetic acid. The mixture was then stirred for 18 hours at 5° C. and the resulting precipitate collected by filtration and washed twice with 100 ml of acetonitrile. The collected solid was slurried in 200 ml of water, collected, washed twice with 50 ml of water and dried under vacuum for 3 days to give 49.7 g of tirapazamine.

EXAMPLE 5

To a stirred mixture containing 1.000 kg (7.347 moles) of benzofuroxan and 2.237 kg (14.694 moles) of DBU was added a solution containing 618 g (14.694 moles) of cyanamide in 380 ml of acetonitrile while maintaining the temperature below 25° C. After stirring for 48 hours at 20–25° C. the reaction mixture was dilute with 6.620 liters of acetonitrile and cooled below 15° C. To the cooled mixture was added 882 g (14.694 moles) of acetic acid while maintaining the temperature below 15° C. After stirring overnight at 5–10° C. the precipitated product was collected by filtration and washed with acetonitrile (2×2 liters). The resulting solid was suspended in 2 liters of water, stirred about 30 minutes until a homogeneous suspension was obtained, and then filtered. The collected solid was resuspended in 2 liters of water, stirred for 20–30 minutes and filtered. The solid collected was dried to constant weight under vacuum at 50–55° C. to give 506.6 g of tirapazamine.

EXAMPLE 6

To a stirred mixture containing 9.5 kg (69.8 moles) of benzofuroxan and 21.3 kg (139.9 moles) of DBU was added a solution containing 5.8 kg (138.0 moles) of cyanamide in 2.7 kg of acetonitrile while maintaining the temperature at 15–25° C. After stirring for 67 hours at 20–25° C. the reaction mixture was diluted with 48 kg of acetonitrile and cooled to 0–10° C. To the cooled mixture was added 8.5 kg (141.5 moles) of acetic acid while maintaining the temperature at 5–15° C. After stirring for 46 hours at 5–10° C., the precipitated product was collected by filtration and washed with acetonitrile (2×15 kg). The resulting solid was suspended in 20 kg of water, stirred for 40 minutes, filtered and the filter cake washed with 10 kg of water. The collected solid was resuspended in 20 kg of water, stirred for 45 minutes, filtered and the filter cake washed with 10 kg of water. The solid collected was suspended in 29 kg of water and to the suspension was added 8.7 kg (90.5 moles) of methanesulfonic acid. The mixture was stirred at 40–50° C. until dissolution was complete. The resulting solution was added to a solution containing 9.2 kg (112.2 moles) of sodium acetate in 49 kg of water and stirred at 10–25° C. for 1.5 hours. The precipitated product was collected by filtration and washed with 10 kg of water. The collected product was suspended in 20 kg of water, stirred for 55 minutes, filtered and the filter cake washed with 10 kg of water. The solid collected was resuspended in 20 kg of water, stirred for 55 minutes, filtered and the filter cake washed with 10 kg of water. The product obtained was dried to constant weight at 50–55° C. to give 4.6 kg of tirapazamine.

What is claimed is:

1. A process for preparing 3-amino-1,2,4-benzotriazine 1,4-dioxide which comprises reacting benzofuroxan with cyanamide in the presence of an organic base in a non-aqueous medium at a temperature of about 20–25° C. followed by treatment with an organic acid.

2. A process according to claim 1 wherein the organic base is selected from the group consisting of DBU and DBN.

3. A process according to claim 2 wherein the organic base is DBU.

4. A process according to claim 3 wherein the organic acid is acetic acid.

5. A process according to claim 1 wherein benzofuroxan is reacted with cyanamide in a ratio of about 2 to 3 moles of cyanamide per mole of benzofuroxan in the presence of an organic base in a ratio of 2 to 3 moles of base per mole of benzofuroxan followed by treatment with an organic acid in a ratio of about 1 to 1.3 moles of acid per mole of base.

6. A process according to claim 5 wherein the base is selected from the group consisting of DBU and DBN.

7. A process according to claim 6 wherein the base is DBU.

8. A process according to claim 7 wherein the organic acid is acetic acid.

9. A process according to claim 8 which is carried out in the presence of a solvent selected from the group consisting of acetonitrile, acetone and isopropanol.

10. A process according to claim 9 wherein the solvent is acetonitrile.

11. A process according to claim 10 wherein benzofuroxan is reacted with cyanamide in a ratio of about 2 moles of cyanamide per mole of benzofuroxan in the presence of DBU in a ratio of about 2 moles of DBU per mole of benzofuroxan in acetonitrile at a temperature of about 20–25° C. followed by treatment with acetic acid in a ratio of about 1 mole of acetic acid per mole of DBU.

12. A process according to claim 11 which comprises the steps of:
   a) reacting benzofuroxan with cyanamide in a ratio of about 2 moles of cyanamide per mole of benzofuroxan in the presence of DBU in a ratio of about 2 moles of DBU per mole of benzofuroxan in acetonitrile in a ratio of about 0.3:1 w/w acetonitrile/benzofuroxan at a temperature of about 20–25° C. for about 48 hours;
   b) diluting the reaction mixture with acetonitrile in a ratio of about 5:1 w/w acetonitrile/benzofuroxan;
   c) treating the reaction mixture with acetic acid in a ratio of about 1 mole of acetic acid per mole of DBU while maintaining the temperature below about 15° C.;
   d) allowing the product to precipitate at about 5–10° C.; and
   e) isolating the 3-amino-1,2,4-benzotriazine 1,4-dioxide from the reaction mixture.

13. A process according to claim 12 further comprising the steps of: dissolving the isolated 3-amino-1,2,4-benzotriazine 1,4-dioxide in aqueous methanesulfonic acid; filtering the solution;
   adding the filtered solution to an aqueous solution of sodium acetate containing about 1 to 1.3 moles of sodium acetate per mole of methanesulfonic acid; and allowing the product to precipitate at about 10–25° C.

* * * * *